Figure 1:
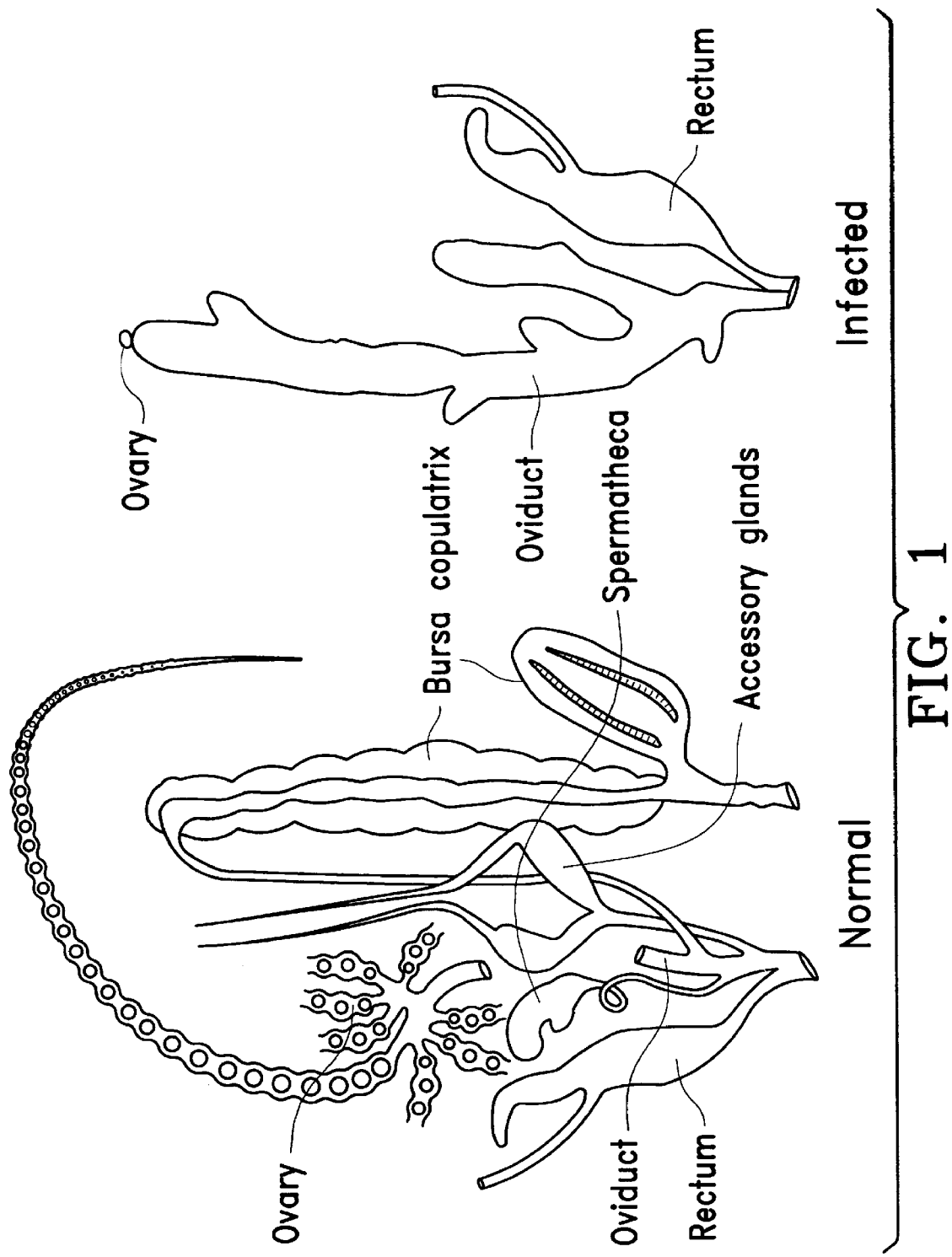

United States Patent [19]
Raina et al.

[11] Patent Number: 5,843,429
[45] Date of Patent: Dec. 1, 1998

[54] GONAD-SPECIFIC VIRUS WHICH CAUSES STERILITY IN THE CORN EARWORM, *HELICOVERPA ZEA*

[75] Inventors: Ashok K. Raina, Beltsville; Jean R. Adams, Hyattsville, both of Md.

[73] Assignee: The United States of America as represented by the Secretary of Agriculture, Washington, D.C.

[21] Appl. No.: 440,158

[22] Filed: May 12, 1995

Related U.S. Application Data

[62] Division of Ser. No. 348,175, Nov. 28, 1994, abandoned.

[51] Int. Cl.$^6$ .......................... A01N 63/00; A01N 25/00; C12N 1/00; C12N 7/00
[52] U.S. Cl. ..................... 424/93.6; 424/405; 435/235.1; 435/243; 435/261; 435/948
[58] Field of Search ................................ 435/235.1, 243, 435/261, 948; 424/405, 93.6

[56] References Cited

U.S. PATENT DOCUMENTS

| 3,541,203 | 11/1970 | Fogle et al. | 424/17 |
|---|---|---|---|
| 5,405,770 | 4/1995 | McIntosh | 435/235.1 |
| 5,420,031 | 5/1995 | Slavicek et al. | 435/235.1 |

FOREIGN PATENT DOCUMENTS

| 53-44889 | 12/1993 | Japan | 435/235.1 |
|---|---|---|---|
| 0025666 | 12/1993 | WIPO | 435/235.1 |
| 0000585 | 1/1994 | WIPO | 435/235.1 |
| 0004660 | 3/1994 | WIPO | 435/235.1 |

OTHER PUBLICATIONS

Degrugillier et al., "J. of Invertebrate Pathology," 61, 147–155 (Mar. 1993).
Leisy et al., "Chemistry & Industry" pp. 250–254 Jun. 1992.
Grandados et al., *Invervirology,* vol. 10, pp. 309–317 (1978).
Stoltz et al., *Can. J. Microbiol.* vol. 22, pp. 1013–1023 (1976).

*Primary Examiner*—David M. Naff
*Assistant Examiner*—Deborah K. Ware
*Attorney, Agent, or Firm*—M. Howard Silverstein; John Fado; Janelle S. Graeter

[57] ABSTRACT

Helicoverpa species constitute the most important group of crop pests throughout the world, and scientists have been pursuing the development of biocontrol agents effective for the control of these pests. A virus, the gonad specific virus (GSV), has been discovered which serves this purpose by infecting Helicoverpa species and generally rendering the insects sterile. Those insects which do not become sterile on infection act as carriers of the virus, spreading it among the insect population and producing infected prog

GONAD-SPECIFIC VIRUS WHICH CAUSES STERILITY IN THE CORN EARWORM, *HELICOVERPA ZEA*

This is a division of application Ser. No. 08/348,175, abandoned filed Nov. 28, 1994.

BACKGROUND OF THE INVENTION

1. Field of the Invention

Biological agents have assumed an important role in the control of crop pests as the effort to reduce or eliminate the use of chemical pesticides has increased. There is thus a strong incentive to discover and develop biological systems which are detrimental to targeted pests but are harmless to the environment. This invention relates to a newly-discovered virus which infects the corn earworm, *Heliocoverpa zea*, and renders it sterile, thereby serving as an effective means for the control of corn earworm and other closely related pests.

2. Description of the Prior Art

Insect infestation of crops is a primary cause of crop loss throughout the United States. A wide variety of chemical pesticides has been relied upon in the past to control insect pests; however, environmental and consumer safety concerns have led to the deregistration of many pesticides and a reluctance to use others on agricultural products which are ultimately intended for human or animal consumption. In addition, many pest species have developed increasing resistance to chemical pesticides, resulting in less susceptibility to pesticidal activity. Scientists thus began to pursue the development of biological control agents which are environmentally safe both from consumer and agricultural perspectives.

The corn earworm *Helicoverpa zea* (*H. zea*) causes an estimated $1.2 billion in crop damage each year and, together with *Helicoverpa armigera* (*H. armigera*) and a related species, *Heliothis virescens* (*H. virescens*), constitutes the most important group of crop pests throughout the world. *H. zea* and *H. armigera* together cause crop damage resulting in losses worth over $5 billion annually. Scientists have therefore been exploring biocontrol methods effective for these pests.

A number of investigators have sought to exploit the natural sex attractants of insects in order to disrupt reproductive behavior. Sekul et al. [*J. Econ. Entomology.* 1975. vol. 68(5), pp. 603–604] identified Z-11-hexadecenal, which is produced and released by the adult female of *H. zea*, and referred to the compound as a sex attractant inhibitor. Sparks et al. (*Southern Cooperative Series Bulletin*. 1988. pp. 50–65) also discussed *Heliothis pheromones* and their potential use as biocontrol agents by mating disruption. Raina et al. (U.S. Pat. No. 5,032,567, 1991) disclosed a neuropeptide referred to as Hez-PBAN. The peptide was isolated from *H. zea* adults, and it activated pheromone biosynthesis in female moths as well as melanization in the larvae. Pheromone production at the wrong time of day can prove hazardous to the females, and larval melanization is often fatal. Kingan et al. (U.S. Pat. No. 5,344,821, 1994) disclosed a pheromonostatic polypeptide obtained from male *H. zea* which, upon injection into the female, stops pheromone production and renders the female unattractive to male insects.

All of these approaches have shown potential for controlling the corn earworm populations by mating disruption; however, consistent success in the field has proven elusive and difficult to achieve for various reasons, such as the lack of an effective carrier or vector. Thus, the need for a reliable, consistently effective means for controlling *H. zea* populations in the field remains an important goal.

SUMMARY OF THE INVENTION

We have discovered a previously unknown virus which, upon infecting the *H. zea* insect, generally renders that insect sterile. The small percentage of infected insects which are not rendered sterile act as carriers of the virus, thus spreading it among the insect population.

In accordance with this discovery, it is an object of the invention to provide a novel virus isolated from *H. zea* which is useful for controlling populations of *H. zea* and related species of pest moths.

It is also an object of the invention to provide a composition comprising the novel virus and an agriculturally acceptable carrier, the composition having effective biocontrol activity.

It is another object of the invention to provide a method of using the novel virus composition for effective control of the targeted insect population.

Other objects and advantages of the invention will become readily apparent from the following description.

BRIEF DESCRIPTION OF THE DRAWINGS

FIG. 1 shows a diagramatic representation of the internal reproductive organs of normal and virus-infected females of *H. zea*.

FIG. 2 shows atypical occlusion bodies (AOBs) of the virus in the lumen of the oviduct. Each AOB contains large numbers of virions.

FIG. 3 shows a high magnification electron micrograph of an AOB showing fine structure of the virions. Each virion has a dense core and an enveloping membrane.

FIG. 4 shows the virus replicating in the nucleus of a cell from the distal portion of the oviduct. A few virions are also seen in the adjoining cytoplasm.

DETAILED DESCRIPTION OF THE INVENTION

Atrophy of gonads in adults of a diapause strain of *H. zea* had been reported in 1982, and the abnormality was attributed to a genetic trait (Herzog and Phillips, *J. Georgia Entomol. Soc.* 1982. vol. 17, pp. 506–513). It has since been observed that between 20–30% of adults of a colony of *H. zea* lacked internal reproductive organs, and a virus was found to be associated with these agonadal (AG) adults. In the female, the common oviduct, which in normal females is 1–2 mm in length, showed uncontrolled growth, and its lumen was filled with milky white. material. Upon examination by electron microscopy, this material was found to contain atypical occlusion bodies (AOBs) having a large number of rod-shaped electrondense nucleocapsids or virions tightly packed in a protein matrix. No polyhedra typical of most baculoviruses were observed.

The infected insects exhibited a lack of most of the internal reproductive organs, such as testes, ovaries and some of their associated structures, and they did not mate. A small percentage of adults in the infected culture did not manifest agonadal symptoms.

There was no abnormal growth or mortality among the various developmental stages of the corn earworm manifesting AG condition. Longevity of AG adults was not significantly different from that of healthy insects. The infected adults did not show any external abnormality except a hypertrophied ovipositor in the females. The pheromone gland (located on the ovipositor) of infected females contained almost 2–3 times more extractable sex pheromone when compared to normal females, and yet there were no attempts to mate. When approached by normal males, the AG females agressively avoided mating.

Internally, in the AG females both the common oviduct and grossly deformed lateral oviducts are almost 100 times the size found in normal females (FIG. 1). The lateral oviducts are profusely covered with fat body and trachea and are full of a white buttery mass of viral AOBs. There are no ovaries except for one or two small yellow structures attached to the distal end of the oviducts that may represent undeveloped larval ovaries. The bursa copulatrix, accessory glands and the spermatheca are also missing.

In the AG males, the endophallus, aedeagus and the ductus ejaculatorius simplex have a normal appearance. In normal males there is a single fused testis giving rise to a pair of seminal vesicles, each connected to vas deferens and duplex. Two long slender accessory glands are connected to the duplexes which lead into a long ductus ejaculatorius simplex (Callahan, P.S., *Ann. Entomol. Soc. Am.* 1958. vol. 51, pp. 413–428; Callahan and Cascio. *Ann. Entomol. Soc. Am.* 1963. vol. 56, pp. 535–556). In the AG males, however, the testes are very small (about the size found in 3rd instar larvae) and not fused. One of the testes is connected to the tip of the ductus ejaculatorius simplex whereas the second is free in the haemocoel. Seminal vesicles, vasa deferentia, duplexes and accessory glands are totally absent. AOBs are present, predominantly in the posterior portion of the ductus ejaculatorius simplex, but are relatively fewer when compared to infected females. The rectum in the majority of AG adults is greatly swollen and filled with fluid containing a large number of bacteria.

Figure 2:
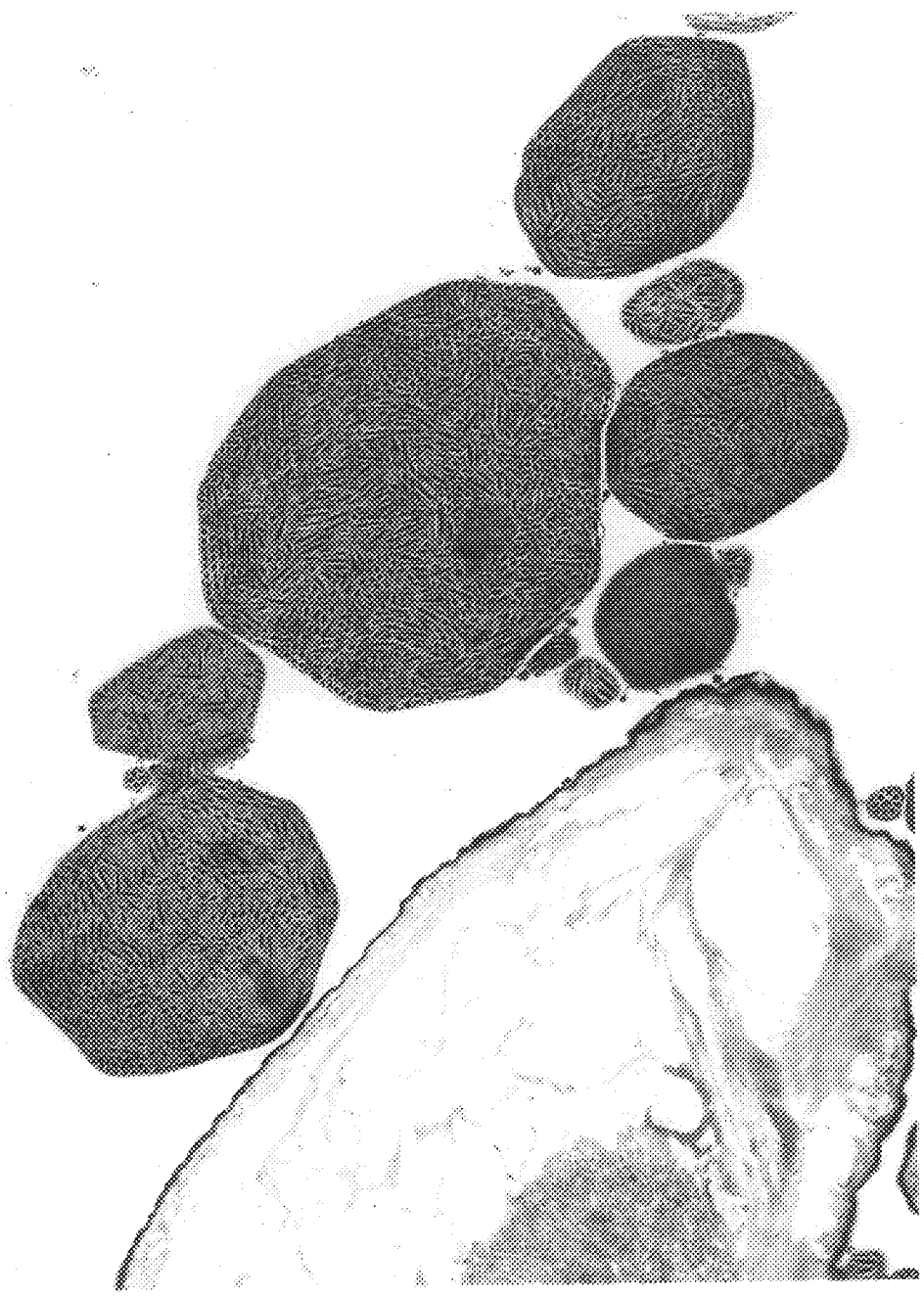
Figure 3:
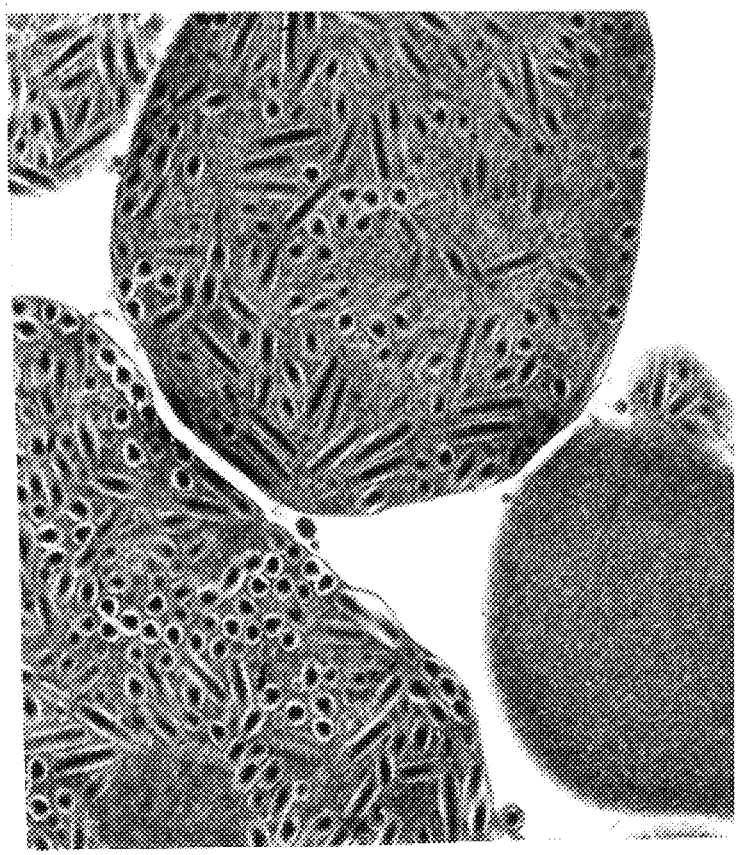
Figure 4:
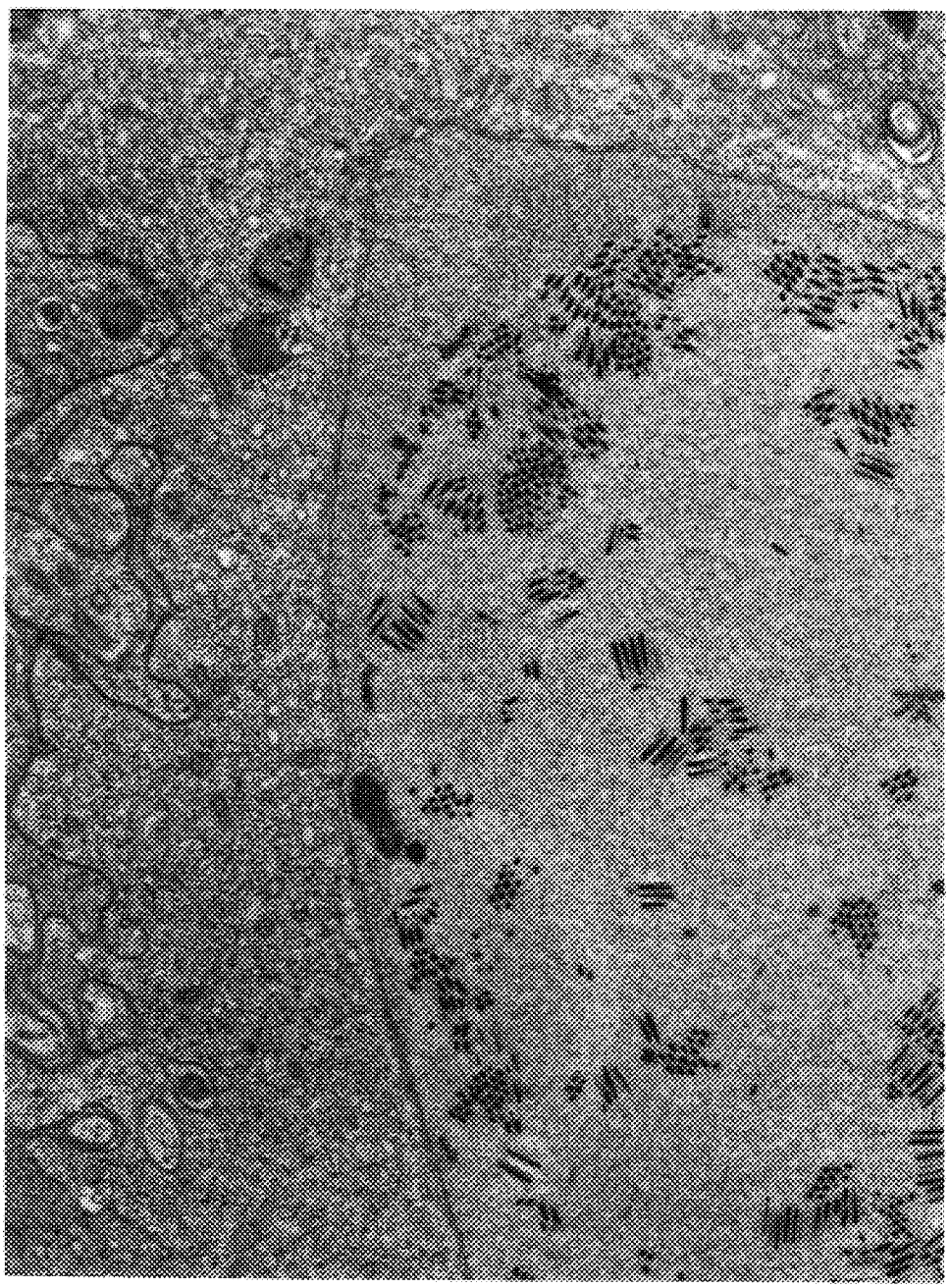

Ultrastructural studies indicated that the virus is confined to the reproductive system and therefore has been designated gonad specific virus (GSV). In the female the lumen of the oviduct was full of AOBs with no visible cytopathology of the adjoining cells (FIG. 2). The AOBs differ from typical nuclear polyhedrosis virus (NPV) in that they contain high concentrations of virions and have a granular protein matrix rather than a polyhedrin protein matrix (FIG. 3). The AOBs also appear to have a host-derived membrane rather than a virus-derived polyhedron-membrane. No typical polyhedra of *H. zea* NPV were observed in other tissues of GSV infected insects, such as tracheal matrix, hypodermis, fat bodies, oviduct and Malpighian tubules. Large numbers of virions were found in the nuclei of cells in the distal part of the oviduct (FIG. 4). Virions were also seen in the cytoplasm, from which clumps of virions budded into the lumen of the oviduct. The virions measured 382±30×77±3 nm (n=50). An insect cell line, IMC-HZ-1, persistently infected with nonoccluded baculovirus-like particles has been reported (Granados et al. *Intervirology.* 1978. vol. 10, pp. 309–317), having virus particles (IMC-HZ-1-NOV) with measurements of 363±62×96±10 nm (n=12), similar to those of GSV. By contrast, the typical *H. zea* NPV infection in fat body tissues (Adams and McClintock in *Atlas of Invertebrate Viruses.* Adams and Bonami, eds. 1991. CRC Press Inc., Boca Raton, Fla., pp. 87–204) produces virions measuring 318±18×42±2 nm (n=50). In addition, biochemical tests using oligo primers designed specifically for the detection of various-baculovirus genes, including the highly conserved polyhedrin gene from the NPV of gypsy moth, indicate that GSV is quite different from typical baculoviruses.

Unlike other known insect baculoviruses, GSV infection could not be established in larvae feeding on a diet smeared with virus collected from the oviduct. All virus fed larvae (n=90) grew to become normal adults, indicating that the virus does not survive and reproduce in the larval gut. Similar results have been reported with the HZ-1-NOV (Granados et al., supra). However, when newly emerged females were fed on a 10% sucrose solution containing the crude virus and allowed to mate on the following day, 25% of the females and 40% of the males in the resulting progeny were AG. Adult moths feed essentially on a liquid carbohydrate diet, therefore they may lack proteolytic enzymes which would destroy the virus, thereby resulting in its survival. Pheromonotropic peptides are also known to survive the passage through adult gut in *H. zea* (Raina et al. *J. Insect Physiol.* 1994. vol. 40, pp. 393–397).

Injection of a crude preparation of GSV at doses as low as 0.001 oviduct eq into the abdomen of newly emerged females, and mating of such females the following day, resulted in progeny showing an average of 76% AG females and 83% AG males.

Immersing *H. zea* eggs in a crude virus solution, however, did not cause the AG condition in the resulting adults, indicating that the virus apparently penetrates the eggs before the chorion is hardened prior to oviposition. The virions of GSV can also be carried by the sperm into the egg at the time of fertilization, suggesting a transovarial mode of transmission.

Infected females with a presumed low titer of GSV do not show the AG symptoms but may act as carriers. GSV can thus be introduced into the natural population of *H. zea* with about 70–80% of the resulting progeny expected to be sterile.

The novel virus was deposited on Aug. 10, 1994 as Gonad Specific Virus of *Helicoverpa zea*, GSV under the Budapest Treaty in the American Type Culture Collection, 12301 Parklawn Drive Rockville, Md. as ATCC No. VR 2471. Upon issuance of a patent, the virus will be irrevocably and without restriction or condition released to the public.

GSV is prepared from oviduct tissue of infected AG *H. zea* females by dissecting out and homogenizing the oviducts. The homogenate is centrifuged, and virus-containing supernatant is removed and stored at −80° C. until further use.

Alternatively, virus may also be grown in cells which have been co-cultured with virus-containing oviduct tissue for a time sufficient for the cells to become infected with the virus. Oviducts dissected from infected AG *H. zea* females are cut up, and pieces of tissue are placed in tissue culture wells containing the cells and an appropriate culture medium. Since the virus is gonad-specific, gonad-derived cells are preferred. Any effective germ cell line is appropriate, however, and it is well within the level of skill in the art to test cell lines to determine their effectiveness for growing the novel virus (see Example I). An example of cells effective for growing the novel virus are *Heliothis virescens* testis, or HvT, cells (as described by Lynn et al., Development of cell lines from various tissues of Lepidoptera. In *Invertebrate and Fish Tissue Culture*. Kuroda et al., eds. 1988. Japan Scientific Societies Press, Tokyo/Springer-Verlag, Berlin, herein incorporated by reference). The virus is secreted into the tissue culture medium by the infected cells and is conveniently harvested by removing the medium from the cells and freezing at −80° C until further use.

Application of GSV as a biocontrol agent may be accomplished by injecting newly emerged *H. zea* females with GSV at approximately $10^{-4}$ oviduct equivalent in about 10 μl PBS. Virus amounts in the range of approximately about $10^{-2}$ to about $10^{-5}$ oviduct equivalents per 10 μl have been found to be effective. An amount of about $10^{-3}$ has been found to result in 100% infectivity. Lower amounts may be advantageous in some circumstances in that the infected insects are more likely to become carriers of the virus and subsequently serve as effective vectors. The preferred concentration for this purpose is approximately about $10^{-5}$ oviduct equivalents. After one day the females are mated to normal males, and eggs are collected for several days. The resulting larvae are placed on an artificial diet (Southland Products, Lake Village, AK) and reared to the pupal stage, at which time the insects are sexed. Adult insects are released in a corn or other *H. zea*-infested field and will mate with the native population thereby spreading the virus, since a majority of the adults are reproductively normal but are carriers of the virus.

Alternatively, a composition of semipurified virus, prepared as described, in a sugar solution such as sucrose and water can be placed in feeding stations in infested fields. Females feeding on the virus-laced sugar solution become carriers of the virus, resulting in progeny showing a significant number of infected adults.

The following examples are intended only to further illustrate the invention and are not intended to limit the scope of the invention as defined by the claims.

EXAMPLES

Example I
Preparation of GSV from Cultured *H. zea* Oviduct Tissue

Infected females were chilled at 4° C., surface disinfected by submerging in 70% ethanol for 10 min, then rinsed twice in sterile deionized water. The insects were transferred to modified TNM-FH tissue culture medium (as described by Hink and Strauss, Growth of the *Trichoplusia ni* (TN-368) cell line in suspension culture. In *Invertebrate Tissue Culture: Application in Medicine, Biology and Agriculture*. Durstak and Maramorosch, eds. 1976. Academic Press, NY) supplemented with 50 μg/ml gentamicin sulfate. The oviducts were removed with sterile microsurgical instruments and transferred into 1.0 ml culture medium. Each oviduct was cut into pieces and transferred to a 24-well tissue culture plate (Falcon) containing approximately $1 \times 10^5$ IPLB-HvT1 cells (Lynn et al., supra). When the cells became extremely dense (after approximately 9 weeks), they were passaged according to conventional subculture procedure, using VMF trypsin (Worthington Biochemicals, Freehold, N.J.). Two weeks later the cells were passaged for the second time. At that time some cells were fixed for electron microscopy which confirmed the presence of replicating virus in the nuclei and virions in the cytoplasm. Virus was secreted by the cells into the culture medium and was obtained by removing the culture medium from the wells and freezing at −80° C. until further use.

Example II
Preparation of GSV from Female *H. zea*

Oviducts of GSV infected females of *H. zea* were dissected out into phosphate buffered saline (PBS) and homogenized with a Microson® ultrsasonic cell disrupter in 100 μl PBS/oviduct. The homogenate was centrifuged at 7,000 rpm for 2 min. The supernatant was removed and stored at −80° C. until further use.

We claim:

1. An isolated gonad-specific virus having all of the identifying characteristics as gonad-specific virus (GSV) ATCC No. VR 2471.

2. A biocontrol composition comprising an effective amount of the virus of claim 1 and an agriculturally acceptable carrier.

3. The composition of claim 2, wherein the agriculturally acceptable carrier is a sugar solution.

4. A method for the biological control of adult Helicoverpa species, said method comprising administering an effective amount of the biocontrol composition of claim 2 to cause a gonad-specific infection in said Helicoverpa species.

5. The method of claim 4, wherein said Helicoverpa species is selected from the group consisting of *Helicoverpa zea* and *Helicoverpa armigera*.

* * * * *